United States Patent [19]
Welsh et al.

[11] Patent Number: 5,935,085
[45] Date of Patent: Aug. 10, 1999

[54] METHOD FOR PREPPING A PATIENT FOR AN ENDOSCOPIC PROCEDURE

[75] Inventors: Stephen W. Welsh, 401 Keene St., Columbia, Mo. 65201; David Porat, Newton, Mass.; David L. Stalling, Columbia, Mo.

[73] Assignee: Stephen W. Welsh, Columbia, Mo.

[21] Appl. No.: 08/976,487

[22] Filed: Nov. 24, 1997

[51] Int. Cl.$^6$ ....................................................... A61B 5/00
[52] U.S. Cl. ........................... 600/573; 600/300; 128/898
[58] Field of Search ..................................... 600/300, 584, 600/573; 604/317, 318; 128/898, 897; 356/432, 436, 441, 442; 73/53.01; 422/82.05

[56] References Cited

U.S. PATENT DOCUMENTS

| | | |
|---|---|---|
| 4,003,661 | 1/1977 | Yamano . |
| 4,774,417 | 9/1988 | Houpt . |
| 4,898,462 | 2/1990 | Numata et al. . |
| 4,901,736 | 2/1990 | Huang ....................................... 600/584 |
| 5,119,829 | 6/1992 | Saito et al. ............................... 600/584 |
| 5,772,606 | 6/1998 | Ashibe et al. ............................ 600/584 |

*Primary Examiner*—Linda C. M. Dvorak
*Assistant Examiner*—Bryan K. Yarnell
*Attorney, Agent, or Firm*—Breiner & Breiner

[57] ABSTRACT

A method for prepping a patient for an endoscopic procedure is described. The patient being prepped will consume inert solutions followed by a discharge of fluid into a commode. Light transmitted through the discharged fluid is measured with the procedure continued until the light transmitted reaches a predetermined level. Preferably, the device is disposable.

8 Claims, 3 Drawing Sheets

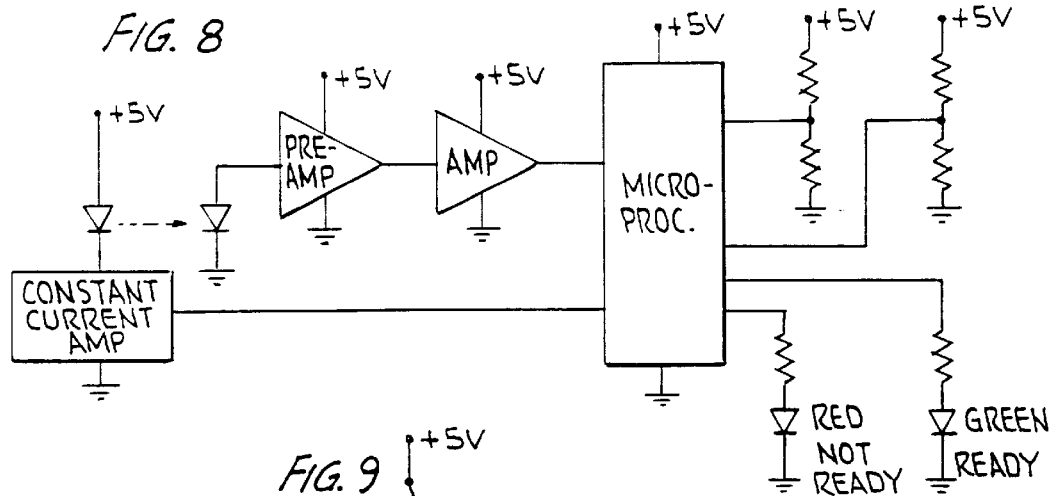
FIG. 8
FIG. 9
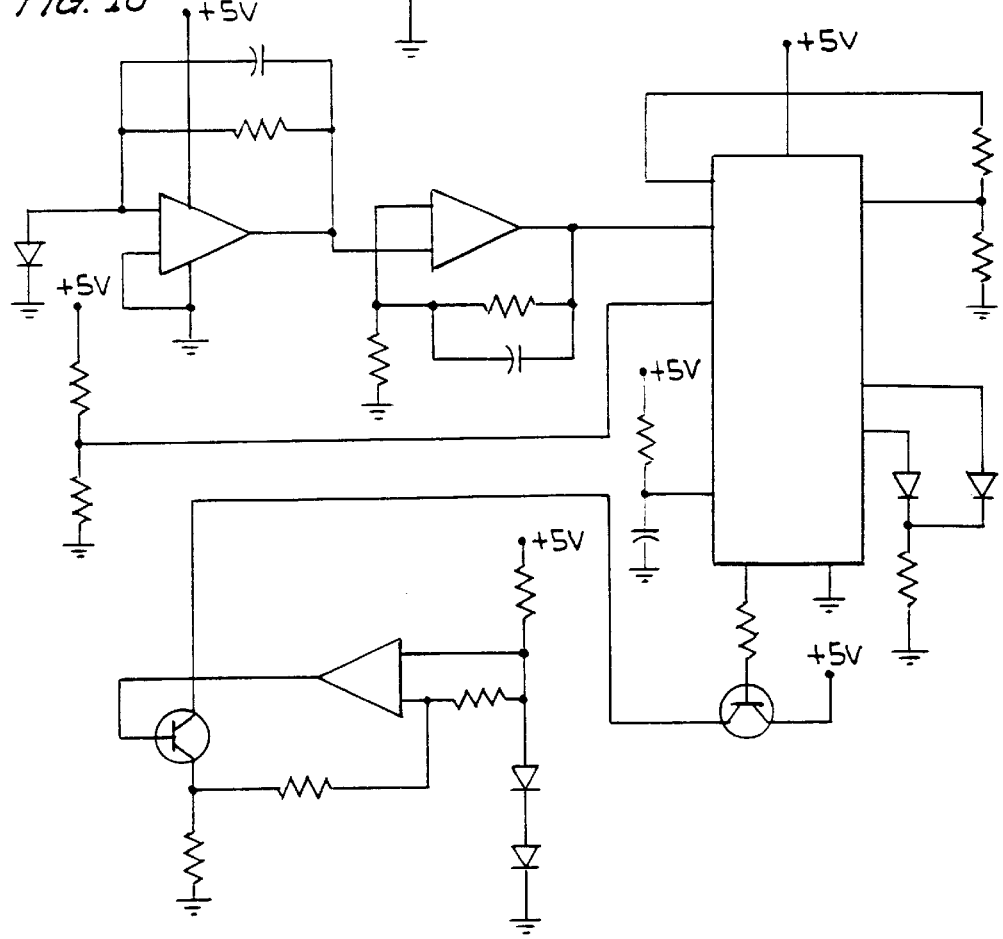
FIG. 10

METHOD FOR PREPPING A PATIENT FOR AN ENDOSCOPIC PROCEDURE

FIELD OF INVENTION

This invention is directed to a method of determining when a patient is sufficiently "clean" to permit an endoscopic procedure and to a device which enables such method to be performed. More particularly, this invention relates to a method which allows a patient that is to undergo an endoscopic procedure, such as a colon procedure, to confirm that the patient has sufficiently cleaned out his or her system prior to reporting to an office, clinic or hospital for the performance of such a procedure, thereby minimizing schedule disruption caused by postponement and/or the need to continue a cleaning/purging procedure at the hospital, clinic or office.

BACKGROUND OF INVENTION

Prior to an endoscopic procedure, such as a colon procedure, a patient, at the direction of the doctor or a nurse, receives enemas and/or takes solutions, such as inert solutions of polyethylene glycol, sorbitol, xenobiotics or the like to clean out the bowels of the patient. This process usually results in the patient consuming 3–6 liters of the solution at home prior to reporting to an office, clinic or hospital where the procedure is to be performed. At the office, clinic or hospital, a nurse confirms that the bowels of the patient are scrupulously clean by measuring (qualitatively) the clarity of the patient's toilet bowl water or performing an examination. If a patient is not sufficiently clean to permit the procedure to go forward, it is necessary to either continue the cleaning/purging procedure at the office, clinic or hospital, causing disruption and delay, or to postpone the endoscopic procedure and send the patient home for further cleaning/purging with it being necessary for the patient to then return.

SUMMARY OF INVENTION

The present invention has as a primary object to provide a method and device which allows a patient to confirm with a high degree of accuracy that the patient has cleaned out his or her digestive system by measuring toilet bowl water clarity and to a device which permits the patient to conveniently perform such method.

Thus, the method of the present invention comprises a patient consuming suitable solutions at home and intermittently, while consuming such solutions, determining the clarity of toilet bowl water and when sufficient clarity is determined, reporting to a hospital, clinic or office for the performance of the endoscopic procedure. The bowl water clarity is determined by a device, preferably disposable, which determines the clarity of bowl water by measuring light transmitted through the bowl water.

In a preferred method, a disposable device is attached to the rim of a toilet bowl with the head of the device including light-transmitting and light-detecting means extending into the bowl water. The device will include means which will transmit light and measure the transmitted light, and indicate automatically when the bowl water is of sufficient clarity to allow performance of the endoscopic procedure.

More specifically, a patient designated to undergo an endoscopic procedure will receive from his or her doctor a disposable unit to enable the patient to determine when his or her digestive system is sufficiently clean to undergo an endoscopic procedure. This unit will be attached to a toilet bowl, preferably the rim of the toilet bowl, so that the head of the unit is submerged in the toilet bowl water. Once so positioned, the unit preferably will remain in place until the entire cleaning or purging of the digestive system is complete. Periodically during the consumption of solutions, the patient will check toilet bowl water clarity by, for example, pressing an activator button on the unit. The unit, through suitable circuitry, will transmit light and measure the transmitted light to determine the turbidity of the bowl water. If turbidity is present in the water, a "red" light will show on the unit. After a time, during the consumption of the solutions, the bowl water will appear clear. If, in fact, the water is clear and transmits a predetermined value of light, a "green" light will show. Preferably, the method will require at least three consecutive green determinations, which will verify that the patient's system is sufficiently clean and it is time for the patient to report to an office, clinic or hospital for the performance of the endoscopic procedure. The unit can be designed so that the patient will press the activator button for each reading. Preferably, however, the unit as designed, once activated, will automatically transmit light and measure the transmitted light at predetermined intervals, for example, each 10 seconds, until the procedure is completed.

It is surprising that transmitted light will provide an adequate determination. Thus, it was originally concluded that it would be necessary to measure both transmitted light (T) and scattered light (S) and determine the S/T ratio. It has now been determined, however, that the most dependable and accurate readings are those based on transmitted light only. For example, it was determined that if the value of transmitted light was at least in the 1700 to 2000 unit range and this reading was obtained for three consecutive determinations, it was safe to carry out the endoscopic procedure. The use of transmitted light only permits the use of simplified electronics. A "unit" as used herein is approximately one-tenth Lux.

THE DRAWING AND DETAILED DESCRIPTION OF THE INVENTION

In the drawing,

FIG. 8 is a simplified circuit diagram showing the electronics of the device of the present invention;

FIG. 9 is a schematic view of the battery pack of the device exemplified in FIG. 8; and FIG. 10 is a detailed view of the circuit diagram shown in FIG. 8 of a preferred embodiment of the invention.

Figure 1:
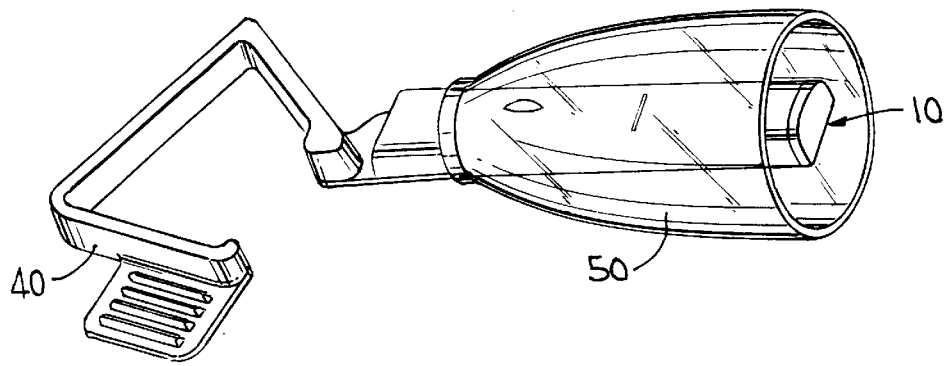
FIG. 1 is a perspective view of a first embodiment of the light-emitting and light-detecting unit according to the invention.

Referring to the drawing, the device of the present invention comprises a light-emitting and light-detecting unit 10, an arm 40 for attaching the device to the rim of a toilet bowl, and shroud 50 partially enclosing the unit to protect the unit during a flushing operation from influences of toilet paper in the commode water.

Figure 2:
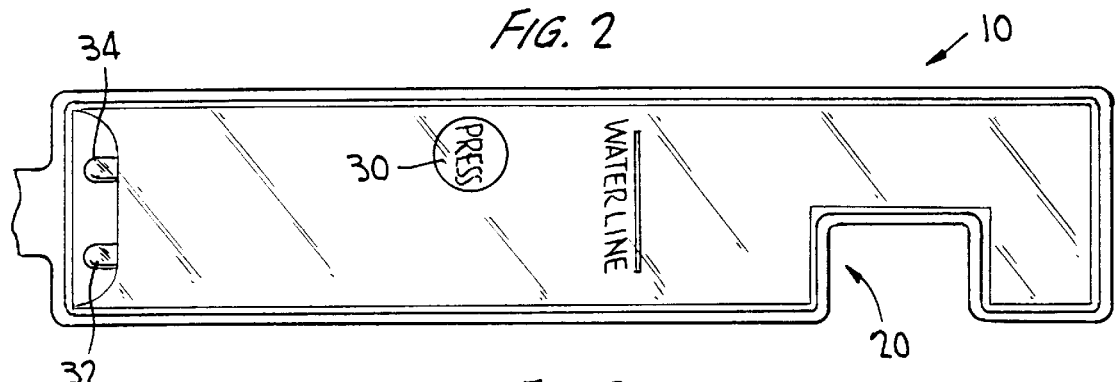
FIG. 2 is a view from the side of the device of FIG. 1 with certain modifications, without the shroud or the attaching arm for attaching the device to a toilet bowl rim as shown in FIG. 1.
Figure 3:
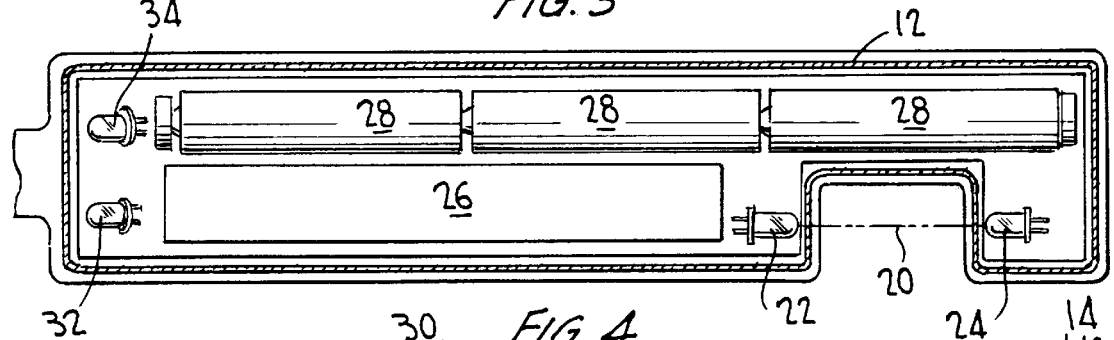
FIG. 3 is a view the same as the view of FIG. 2 with the housing cut-away to show the internal mechanism of the device.
Figure 4:
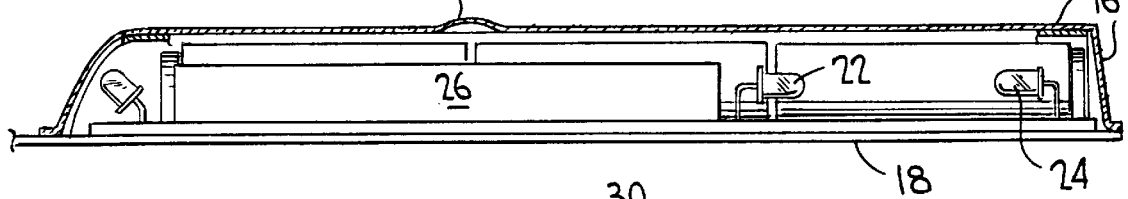
FIG. 4 is a view of the device of FIG. 2 partly in section showing the internal mechanism of the device similar to FIG. 3 but from a different position.
Figure 5:
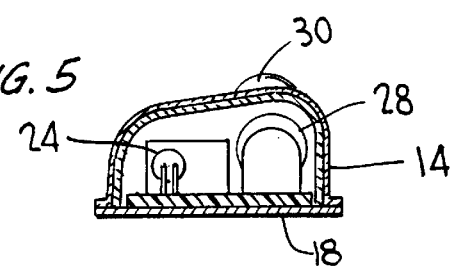
FIG. 5 is an end view partly in section of the device shown in FIG. 4.

Thus, as best shown in FIGS. 2–5, in a first embodiment the light-emitting and light-detecting unit 10 comprises a housing 12 having a U-shaped top member 14, an end member 16, and a bottom member 18. As best shown in FIGS. 2 and 3, the housing has an indented area in the housing of the unit as shown generally at 20. As best shown in FIG. 3, a light-emitting member 22 passes emitted light through the housing into the indented area 20, which light is detected by a detecting member 24. Light transmitted from member 22 to detecting member 24 will determine solid matter within the toilet bowl water.

The unit is controlled by an electronic circuit board diagrammatically shown at 26 and in FIGS. 8 and 10. The unit is powered by three AAA cells 28. The device when positioned in a commode is activated by pressing activator button 30. The unit in a preferred embodiment and as shown in the circuit diagram set forth in FIG. 10, once activated by pressing button 30, will remain activated throughout the useful life of the device which is about 6 to 8 hours. During this time period, in a preferred embodiment, the unit will transmit and measure the transmitted light automatically each 10 seconds, once activated, until the procedure is completed. The circuitry shown in FIG. 10 also includes electronics to adjust the power level to remain constant throughout the checking procedure, thus eliminating any false readings as a result of battery deterioration. The light detected in area 20 by light detector 24 is electronically read and if solid matter beyond a certain level is detected by detector 24 a light 32 will show "red." If solid matter is not detected and the light transmitted exceeds a certain level, a light 34 will show "green." In the event a green light is obtained for three consecutive readings, it is assumed that the gastro-intestinal system is clear and the patient can undergo an endoscopic procedure. It has been found that if the measured light exceeds about 1700 units the endoscopic procedure can be safely performed.

Figure 6:
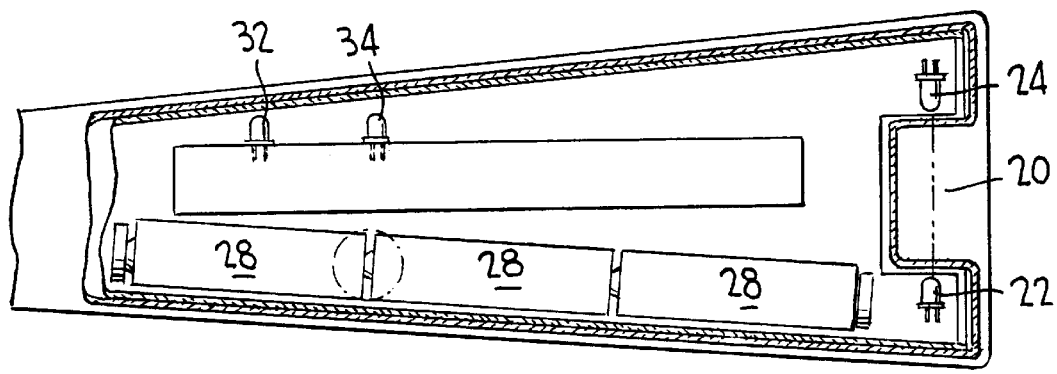
FIG. 6 is a partially cut-away view of a second embodiment of the light-emitting and light-detecting unit of the invention.

FIG. 6 illustrates a modified device containing all of the componentry of the device of FIGS. 2–5. However, the device is modified to the extent that it is in the form of a trapezoid with the window for receiving commode water, shown generally at 20, being in the end of the unit rather than on the side of the unit. Otherwise the device is the same.

Figure 7:
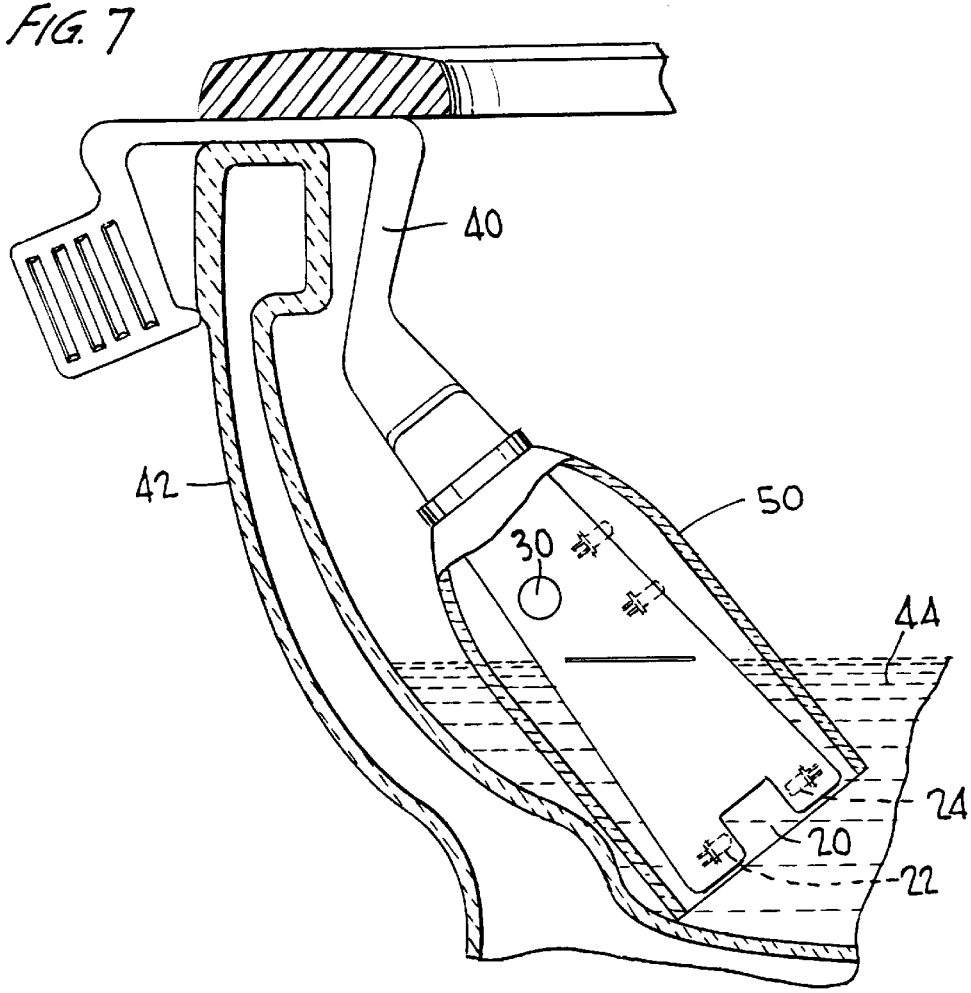
FIG. 7 is a view partially in section of the device of FIG. 6 including the shroud and attaching arm with the unit positioned in a commode as in use.

As illustrated in FIG. 7, the device of FIG. 6 is positioned on the rim 42 of a toilet bowl by arm 40. The design of the arm is such that when positioned on the rim the device is suspended in toilet bowl water 44 at a level where the light-emitting member 22 and the light-detecting member 24 are submerged in the toilet bowl water. The shroud 50, as best shown in FIG. 7, completely surrounds the light-emitting and light-detecting unit 10 to prevent interference of the device by toilet paper within the bowl water during the flushing operation. The device, as shown, is compact and of simplified design to permit construction and utilization as a disposable unit. In this way, once the unit is used by a patient it is discarded, protecting against contamination and spreading of communicable diseases by patients.

As will be apparent to one skilled in the art, various modifications can be made within the scope of the aforesaid description of the invention, such modifications being within the ability of one skilled in the art form a part of the present invention and are embraced by the appended claims.

It is claimed:

1. A method of prepping a patient for an endoscopic procedure comprising (1)providing a light unit with a light transmitting means for transmitting light and a light sensing means for measuring light; (2)consuming a first volume of an inert solution; (3)measuring the light transmitted through fluid discharged after step 2 with said light unit; (4)consuming an additional volume of said inert solution; (5)measuring the light transmitted through fluid discharged after step 4; and (6)continuing steps 4 and 5 until light transmitted through fluid discharged after repeating step 4 exceeds a predetermined value.

2. The method of claim 1 wherein said predetermined value of transmitted light in step 6 is at least 1700 units.

3. The method of claim 2 wherein the transmitted light of step 6 remains constant within a range of plus or minus 50 units for three consecutive measurements after steps 4 and 5.

4. The method of claim 3 wherein said transmitted light measurements are carried out with a disposable unit having light-transmitting and light-sensing means, with said light-transmitting means being disposed in said discharged fluid.

5. The method of claim 4 wherein said light-transmitting and light-sensing means of said disposable unit includes a light-emitting diode (LED) and said transmitted light is emitted from said LED.

6. Method of prepping a patient for an endoscopic procedure comprising (1) positioning a disposable unit comprising light-transmitting and light-measuring means in a toilet bowl so that said light-transmitting means is submerged in toilet bowl water, said positioning being such that said disposable unit remains so positioned through a series of flushings of said toilet bowl; (2) consuming a first volume of a inert solution; (3) measuring light transmission through fluid discharged into said toilet bowl water after step 2; (4) consuming an additional volume of said inert solution; and (5) measuring the light transmitted through fluid discharged after step 4 and repeating steps 4 and 5 until light transmitted through fluid discharged after step 5 exceeds a predetermined value.

7. The method of claim 6 wherein said predetermined value of transmitted light in step 5 is at least 1700 units.

8. The method of claim 7 wherein the transmitted light of step 5 remains constant within a range of plus or minus 50 units for three consecutive measurements after steps 3 and 4.

* * * * *